(12) United States Patent
Schiller et al.

(10) Patent No.: US 10,143,790 B2
(45) Date of Patent: Dec. 4, 2018

(54) PORTABLE DIALYSIS DEVICE

(75) Inventors: Wolfgang Schiller, Bonn (DE);
Thomas Schmid, Herrsching (DE)

(73) Assignee: NEPHRODITE, LLC, Wilmington, DE (US)

( * ) Notice: Subject to any disclaimer, the term of this patent is extended or adjusted under 35 U.S.C. 154(b) by 599 days.

(21) Appl. No.: 14/125,218

(22) PCT Filed: Jun. 8, 2012

(86) PCT No.: PCT/EP2012/060867
§ 371 (c)(1),
(2), (4) Date: Mar. 6, 2014

(87) PCT Pub. No.: WO2012/168412
PCT Pub. Date: Dec. 13, 2012

(65) Prior Publication Data
US 2014/0202958 A1    Jul. 24, 2014

(30) Foreign Application Priority Data
Jun. 10, 2011   (DE) .................. 10 2011 103 932

(51) Int. Cl.
*A61M 1/16*   (2006.01)
*A61M 1/10*   (2006.01)
*A61M 1/26*   (2006.01)

(52) U.S. Cl.
CPC ........ *A61M 1/1621* (2014.02); *A61M 1/1037* (2013.01); *A61M 1/1631* (2014.02);
(Continued)

(58) Field of Classification Search
CPC .. A61M 1/1037; A61M 1/106; A61M 1/1621; A61M 1/1631; A61M 1/1649;
(Continued)

(56) References Cited

U.S. PATENT DOCUMENTS 5,397,354 A * 3/1995 Wilk ................ A61F 2/022
604/28
6,607,368 B1   8/2003 Ross et al.
(Continued)

FOREIGN PATENT DOCUMENTS

DE   19821543 A1   11/1999
DE   102006035798 A1   2/2008
FR   2276856 A1   1/1976

OTHER PUBLICATIONS

International Search Report dated Oct. 15, 2012 for PCT application No. PCT/EP2012/060867.
(Continued)

*Primary Examiner* — Dirk R Bass
(74) *Attorney, Agent, or Firm* — Ohlandt, Greeley, Ruggiero & Perle, LLP

(57) ABSTRACT

A portable dialysis device that can be continuously worn in and/or on the body of a patient, with a blood chamber in which the patient's blood can be received, a hydraulic chamber which can be filled with a hydraulic fluid and which adjoins the blood chamber, an at least partially flexible delivery membrane which is arranged between the hydraulic chamber and the blood chamber and which, when the hydraulic chamber is filled with hydraulic fluid, is movable in the direction of the blood chamber in such a way as to cause a compression of the blood chamber and therefore an ejection of the blood located therein, a pump for controllable filling and/or emptying of the hydraulic fluid in the hydraulic chamber, such that blood can in this way be conveyed into the blood chamber and/or out of the latter, a filter membrane which is arranged between the blood chamber and the hydraulic chamber and through which waste substances in the blood can be removed to the hydraulic fluid located in the hydraulic chamber, such that the hydraulic fluid serves at (Continued)

the same time as dialysate. Additionally, a method for operating a portable dialysis device.

14 Claims, 3 Drawing Sheets

(52) U.S. Cl.
CPC ........ *A61M 1/1649* (2014.02); *A61M 1/1678* (2013.01); *A61M 1/267* (2014.02); *A61M 1/106* (2013.01); *A61M 2209/088* (2013.01)

(58) Field of Classification Search
CPC ................ A61M 1/1678; A61M 1/267; A61M 2209/088
USPC .................... 210/137, 201, 206, 646; 604/27
See application file for complete search history.

(56) References Cited

U.S. PATENT DOCUMENTS

| | | | |
|---|---|---|---|
| 2003/0134416 A1* | 7/2003 | Yamanishi | A61M 1/36 435/372 |
| 2004/0254514 A1* | 12/2004 | Gura | A61M 1/16 604/5.01 |
| 2006/0030809 A1 | 2/2006 | Barzilay et al. | |
| 2006/0253194 A1 | 11/2006 | Dial | |

OTHER PUBLICATIONS

Written Opinion Report dated Oct. 15, 2012 for PCT application No. PCT/EP2012/060867.

\* cited by examiner

PORTABLE DIALYSIS DEVICE

BACKGROUND

1. Field of the Disclosure

The disclosure relates to a portable dialysis device, as well as to a method for operating such a device.

2. Discussion of the Background Art

Worldwide, there is a very high number of patients that suffer from kidney diseases and need a kidney replacement therapy. Presently, the major part of kidney replacement therapies takes the form of dialysis treatments. Here, an exchange of substances occurs via a membrane, with blood or plasma on the one side of the membrane and a dialysate on the other side of the membrane.

On the one hand, dialysis occurs by way of diffusion. Diffusion means an exchange of particles from that side of the membrane having the higher particle concentration to the side having the lower concentration. Thus, a concentration gradient must exist for a diffusion to be performed.

Further, dialysis uses the principle of ultrafiltration wherein liquids and/or particles pass through the membrane owing to a pressure gradient.

In addition to the aspects mentioned, osmotic effects may also be used in dialysis.

Presently known dialysis methods require very large membrane surfaces, since a blood purification effect is intended to be achieved in a relatively short time (e.g., three times a week for 4 to 6 hours). Presently known dialyzers address this problem by using a plurality of membrane tubes with a very small diameter through which the blood is directed. Despite these large membrane surfaces, it is necessary for the patient to observe the above-mentioned times several times a week. Another problem of dialysis methods known from prior art is that a large vessel port is required that can ensure the necessary large volume flow. For this purpose, arterio-venous shunts are placed, for example, which act as a "short-circuit" between an artery and a vena of the patient. Such shunts represent high stress for the cardiovascular system of the patient.

It is an object of the disclosure to provide a method and a device that allow a comfortable dialysis.

SUMMARY

The portable dialysis device can be carried continuously either in or on the body of a patient. It comprises a blood chamber which can hold blood of a patient. Further, it comprises a hydraulic chamber adapted to be filled with a hydraulic fluid and adjoining the blood chamber. An at least partially flexible delivery membrane is arranged between the hydraulic chamber and the blood chamber. In this context, flexible means that the shape of the delivery membrane can be changed such that at least a part thereof can be displaced towards the blood chamber or towards the hydraulic chamber. Thus, the delivery membrane separates the blood chamber from the hydraulic chamber. During the process of filling the hydraulic chamber with hydraulic fluid, the delivery membrane can be moved towards the blood chamber such that a compression of the blood chamber and thus an expulsion of the blood contained therein occur.

The dialysis device further comprises a pump for a controllable filling and/or emptying of the hydraulic fluid in the hydraulic chamber so that blood can thereby be conveyed into and/or out of the blood chamber.

Further, a filter membrane is arranged between the blood chamber and the hydraulic chamber, through which membrane the waste substances can be discharged into the hydraulic fluid in the hydraulic chamber so that the hydraulic fluid at the same time serves as the dialysate.

The portable dialysis device of the present disclosure allows for a continuous round-the-clock dialysis in or on the body of a patient. Owing to this continuous dialysis, the necessary membrane surface can be reduced significantly as compared to known dialysis devices. For example, the dialysis device of the present disclosure may comprise a filter membrane with a membrane surface of 2 $cm^2$ to 200 $cm^2$, in particular 5 $cm^2$ to 50 $cm^2$. It is important in performing a continuous round-the-clock dialysis to provide a continuous exchange of the blood to be purified. According to the disclosure, a pump is used for that purpose. However, the blood of the patient is not conveyed directly by the pump, since the mechanical loads existing during pumping would cause damage to the substances in the blood. Instead, a compressible blood chamber is provided that is compressed by a flexible membrane. The membrane is moved towards the blood chamber by filling the hydraulic chamber, which adjoins the blood chamber, with a hydraulic fluid conveyed by the pump. By controlling the pump correspondingly, it is thus possible to control the conveying velocity, the conveying frequency and the conveying pressure at which the blood is conveyed into and out from the blood chamber. This allows for an exact control of the dialysis process.

An essential feature of the portable dialysis device of the disclosure is the use of the hydraulic fluid, which causes the compression of the blood chamber, as the dialysate. In other words, a liquid is used as the hydraulic fluid, which is used as the dialysate in presently known dialysis devices. Waste substances, which are to be removed from the blood by the dialysis, can thus pass from the blood in the blood chamber through the filter membrane into the dialysate in the hydraulic chamber. This can be achieved by means of diffusion or osmotic processes using a concentration gradient and/or by means of ultrafiltration using a pressure gradient. With ultrafiltration, it is particularly advantageous that by using the pump in the dialysis device of the disclosure, the pressure gradient between the pressure chamber and the dialysis chamber can be adjusted precisely.

Thus, the disclosure has achieved to provide a very compact dialysis device that can be carried permanently in or on a patient's body so that a permanent dialysis can be performed. This, in turn, allows for a significant reduction of the required membrane surface for the dialysis. Time-consuming visits to a dialysis centre, as they have been necessary up to the present, can thus be omitted. Further, placing a shunt that is necessary in the known dialysis methods can be dispensed with. The stress on the cardiovascular system of the patient is thus significantly reduced.

In order to prevent the blood from the blood chamber, which has just been purified, to mix with fresh blood not purified, it is possible to use a separate inlet and outlet for the blood chamber with respective separate valves. When filling the blood chamber, the inlet valve of the inlet can be opened so that the blood chamber is filled with fresh blood not yet purified, while the valve is closed to expel the blood from the blood chamber after purification. For this purpose, the outlet valve of the outlet is opened.

As an alternative, it is possible to provide a common inlet and outlet for the blood chamber, which is disposed as close as possible to the blood vessel with which the dialysis device is connected. Due to the continuous blood flow in the blood vessel, the purified blood expelled from the blood chamber is conveyed further so that, when the blood chamber is filled the next time, it is filled mostly with fresh, not purified blood from the blood vessel. It is important in this context that the dead volume, i.e. the volume in the supply line from the blood vessel to the blood chamber is as small as possible, since no blood circulation occurs there.

Preferably, no further connection other than the connection via the filter membrane exists between the blood chamber and the hydraulic chamber, via which an in particular direct exchange of liquids or particles would be possible. For the purpose of receiving blood, adapters known from prior art can be used to connect the blood chamber to the cardiovascular system of the patient, e.g. to the aorta or to the venous system. Commercially available vascular prostheses can be used for this purpose.

In a preferred embodiment the filter membrane and the conveying membrane are the same component so that the filter and conveying membrane at the same time compresses the blood chamber and filters the blood. For this purpose the filter membrane may comprise pores, for instance, through which waste substances that are to be removed from the blood can pass from the blood chamber into the hydraulic chamber. In the context of the present disclosure waste substances to be removed from the blood are those substances that are also removed from the blood in known dialysis processes, such as urinary excreted substances, nephrotoxines and electrolytes. The pore size of the filter membrane is such that the mentioned substances are transmitted, but larger molecules such as proteins and blood cells are held back. Further, the dialysis device of the present disclosure makes it possible to extract liquid from the blood of a patient by applying a pressure gradient (i.e. by generating a vacuum on the dialysate side). By inverting this pressure gradient, it is further possible, according to the disclosure, to supply this liquid to the patient again.

In an alternative embodiment, the filter membrane and the conveying membrane are designed as separate components. In this embodiment the filter membrane may be inflexible, for example, since it is not used to compress the blood chamber.

It is further preferred that the rotary direction of the pump can be reversed. Moreover, it is preferred that the volume flow of the hydraulic fluid conveyed by the pump is controllable. Thus, by means of the pump or assisted by the pump, blood can be conveyed into and out from the blood chamber as a defined volume flow.

By controlling the volume flow of the hydraulic fluid conveyed by the pump, the pressure gradient between the blood and the hydraulic fluid serving as the dialysate can be adjusted for controlling the blood purification by ultrafiltration, by setting the pressure in the hydraulic chamber to a higher or lower value than in the blood chamber.

It is further preferred that the pump provides a continuous conveying of blood without interruption into the blood chamber and out of the latter, wherein in particular the volume flow of the blood conveyed into the blood chamber is 0.4 l to 2.5 l, in particular 0.8 l to 1.5 l per minute for adult patients and 50 ml to 800 ml, in particular 100 ml to 400 ml per minute for children.

It is further preferred that the blood chamber and the hydraulic chamber are arranged in an incompressible housing. Further, the blood chamber may comprise an incompressible section at the inlet side, which at the downstream end thereof, seen in the direction of the blood inlet flow, is formed with a flow breakaway edge at which the blood chamber widens abruptly, in particular at an angle of at least 90" relative to the extension of the inlet-side incompressible section of the blood chamber. At this position in the blood chamber, it is thus possible to enhance a return flow of blood from the blood chamber while avoiding dead points in the flow. Dead points in the flow in the blood chamber are a significant risk, since they may cause the formation of thrombi. Owing to the above mentioned flow-optimized design of the blood chamber by means of the flow breakaway edge downstream of the inlet-side incompressible section of the blood chamber, an optimized blood flow can be achieved.

In another preferred embodiment the device comprises an in particular implantable or partially implantable reservoir for receiving a larger volume of the hydraulic fluid serving as the dialysate than the hydraulic chamber does receive. This means that the reservoir can hold a larger volume of hydraulic fluid than the hydraulic camber. The hydraulic fluid may be pumped from the reservoir to the hydraulic chamber and back in particular by means of the pump. When hydraulic fluid is conveyed from the reservoir to the hydraulic chamber, the concentration of waste substances in the hydraulic fluid contained in the hydraulic chamber is reduced. Thus, the concentration gradient between the blood and the dialysate in the hydraulic chamber can be maintained for a longer period of time, so that a particle exchange by diffusion s possible for a longer period of time.

It is preferred that the reservoir comprises a discharge device for discharging dialysate from the reservoir. This may, for example, be a connection to the urinary system and/or the colon of the patient, so that the liquid in the reservoir is excreted by the patient in a natural manner. For example, the connection to the ureter of a patient can be controllable by means of a control valve, wherein the filling level of the dialysate in the reservoir can be determined using a level sensor. The control valve for establishing a fluid communication between the reservoir and the urinary system of the patient can be activated, for example, by means of an external control unit or by means of an integrated control. In this context it is preferred that the volume of the liquid discharged can be controlled so that an excessive loss of liquid of the patient is prevented. If the reservoir is connected with the urinary system of the patient, the sutures required for this purpose can be coated in order to avoid the formation of urinary stones.

Further, it is possible to bind the waste substances in the dialysate contained in the reservoir to larger particles using physical or chemical processes, the reservoir may comprises a filter through which water can pass, but which cannot be permeated by the waste substances bound to the larger particles. Thus, it is possible to discharge water from the reservoir, in particular in a continuous manner, whereas the waste substances can be removed less frequently, e.g. once a week. This may be done, for example, by puncturing the reservoir at a corresponding port known from prior art. As an alternative it is possible to discharge the entire liquid from the reservoir at regular intervals so that the concentration gradient between the blood and the dialysate can be maintained for a long period of time.

In an alternative embodiment the dialysis device comprises a second blood chamber, a second hydraulic chamber, a second delivery membrane and a second filter membrane, which cooperate in a manner corresponding to the first blood chamber, the first hydraulic chamber, the first delivery membrane and the first filter membrane. In this case, it is possible to alternately or simultaneously convey hydraulic fluid into and out of the first and second hydraulic chambers so that a simultaneous or alternate compression and expansion of the first and second blood chambers occurs. In this embodiment of the device the pore sizes of the first and second filter membranes differ from each other. Besides the pore size, other membrane properties such as the pore density and/or the pore shape, for instance, can also be different. For example, it is possible that the first filter membrane has a large pore size so that it can be passed by a great number of substances present in the blood. By generating a vacuum in the first hydraulic chamber by means of the pump, these substances are made to pass from the blood in the blood chamber into the dialysate in the hydraulic chamber. The vacuum in the first hydraulic chamber can be generated by the pump pumping hydraulic fluid from the first hydraulic chamber. By pumping this hydraulic fluid, at the same time serving as the dialysate, from the first hydraulic chamber, the same is supplied to the second hydraulic chamber. In the latter, the pump generates an overpressure so that a part of the substances in the dialysate can be passed through the second filter membrane into the blood in the second blood chamber. For a selective transfer of these substances into the blood, the second filter membrane may, for example, have smaller pores than the first filter membrane so that those substances that must not get into the blood are retained in the dialysate.

Moreover, the device of the disclosure may comprise at least one sensor for determining the systole in the circulation of the patient. Thereby, the pump can be controlled such that the supply of blood into the blood chamber occurs during the systole so that the conveying function of the natural blood circulation is utilized.

In another preferred embodiment, the device comprises a first pressure plate arranged between the blood chamber and the hydraulic chamber and displaceable from the hydraulic chamber towards the blood chamber as the hydraulic chamber is filled with hydraulic fluid, so that the pressure plate causes a compression of the blood chamber. Thereby, a uniform compression of the blood chamber can be achieved.

The device may further include a charge generator device for the generation of an electric charge, for instance in the filter membrane or at another component. The electric charge causes a repulsion of waste products in the hydraulic fluid so that they are prevented from flowing towards the filter membrane. Thereby, a return flow of these waste products into the blood is prevented. For example, it is possible to apply a negative electric charge at the filter membrane or another component so that negatively charged molecules in the blood such as proteins are repelled. Thereby, they are firstly prevented from permeating the membrane and can secondly not settle in the pores of the membrane and clog the same thereby.

In another preferred embodiment the hydraulic chamber adjoining the blood chamber is a first hydraulic chamber. By means of a pump, the hydraulic fluid can be conveyed from this first hydraulic chamber into a second hydraulic chamber and back from the same. The pump may be the same pump that has been described before. The second hydraulic chamber adjoins a secondary dialysate chamber and is separated therefrom by a second filter membrane through which waste products can be discharged from the hydraulic fluid, serving as the dialysate, to the secondary dialysate in the secondary dialysate chamber. In this embodiment, first, a passage of waste products from the blood through the first filter membrane towards the hydraulic fluid or the dialysate occurs. The latter thus is a primary dialysate. The primary dialysate can also contain substances that are meant to be returned into the blood, e.g. plasma. With regard to the pore size, the first filter membrane is designed such that these substances can pass the first filter membrane. However, these substances cannot pass the second filter membrane, since it has a smaller pore size. Corresponding to the first filter membrane, the second filter membrane may also serve as the delivery membrane and covey the secondary dialysate into and out of the secondary dialysate chamber. Thus, a continuous exchange of the secondary dialysate occurs in the secondary dialysate chamber.

For the purpose of conveying the hydraulic fluid, suitable miniature pumps can be used that may be designed, for example, as axial, diagonal or displacement pumps. For instance, roller pumps or vane pumps can be used. It is also possible to use a piston pump or an axial drive. The pump may be arranged immediately in the housing of the dialysis device or in the reservoir. By using a pump to convey blood into the blood chamber and from the same, it can be ensured that a continuous exchange of the blood in the blood chamber occurs so that an efficient dialysis can be performed.

For the energy supply of the implant, a core-less, in particular flexible receiver coil can be provided that can be coupled to an extracorporeal, in particular also flexible transmitter coil so that energy is inductively supplied to the implant. In this manner, it is possible to avoid an energy supply of the implant via transcutaneous power lines.

In another preferred embodiment the delivery membrane is designed such that only a part of the blood volume can be expelled from the blood chamber. In this embodiment the blood chamber may, for example, comprise a separate inlet and a separate outlet that are located on the same side of the blood chamber. Thus, the blood flows through the inlet into the blood chamber, wherein the flow of the blood in the blood chamber may take the shape of a lower case y. In this case, the inlet and the outlet are at the two upper ends of the lower case y. Thereby, a particularly flow-optimized design of the blood chamber can be achieved. It is preferred that in all embodiments of the disclosure a residual volume always remains in the blood chamber so that the blood chamber is never fully emptied. Thus, a mechanical damage to a blood film always present in the blood chamber can be avoided.

For the determination of the systole in the circulation of the patient, one may, for example, refer to the motor current curve of the pump used in the dialysis device so that no additional sensors are required. At a low power consumption of the pump, one may assume the diastole, for example, whereas a high power consumption of the pump indicates the systole.

It is further possible to design the blood chamber such that it is compressed from both sides. For this purpose, one hydraulic chamber is disposed on either side of the blood chamber. As an alternative, a single hydraulic chamber may also comprise the blood chamber and compress the same from both sides. Thus, it is possible to expel the blood volume from the blood chamber in a uniform manner.

The disclosure further refers to a method for operating a portable dialysis device, the method having the following steps:

First, the hydraulic chamber is continuously and alternately filled and emptied by the pump.

When the hydraulic chamber is filled, an at least partly flexible delivery membrane is moved towards a blood chamber adjoining the hydraulic chamber, whereby the former is compressed. When the hydraulic chamber is emptied, the delivery membrane is moved from the blood chamber so that the latter expands.

Thus, a continuous and alternating compression and expansion of the blood chamber by the delivery membrane occurs such that a continuous uninterrupted exchange of the blood in the blood chamber occurs.

The method of the present disclosure may include all features described in the context of the device of the present disclosure, and vice versa.

The method may further comprise the following additional steps:

The systole and/or the diastole in the circulation of the patient can be detected by at least one sensor. Instead of a sensor, the systole and the diastole can also be determined from the motor current of the pump of the device of the present disclosure. During the diastole, hydraulic fluid is pumped into the hydraulic chamber. As an alternative or in addition, hydraulic fluid can be pumped from the hydraulic chamber during the systole so that the blood chamber is filled with blood during the systole and the blood chamber is emptied into the circulatory system of the patient during the diastole.

Further, it is possible to bind waste products in the dialysate contained in the hydraulic chamber, which are not supposed to return into the blood via the filter membrane, to larger particles in a chemical or physical manner, which particles cannot pass the filter membrane due to their size.

The disclosure further refers to the use of a dialysate of a dialysis device as the hydraulic liquid for the alternating compression and expansion of a blood chamber by means of a delivery membrane, wherein the blood chamber comprises a filter membrane for discharging waste substances from the blood into the dialysate on the other side of the filter membrane.

The following is a detailed description of preferred embodiments of the disclosure with reference to the drawings.

DETAILED DESCRIPTION OF THE PREFERRED EMBODIMENT

Figure 1:
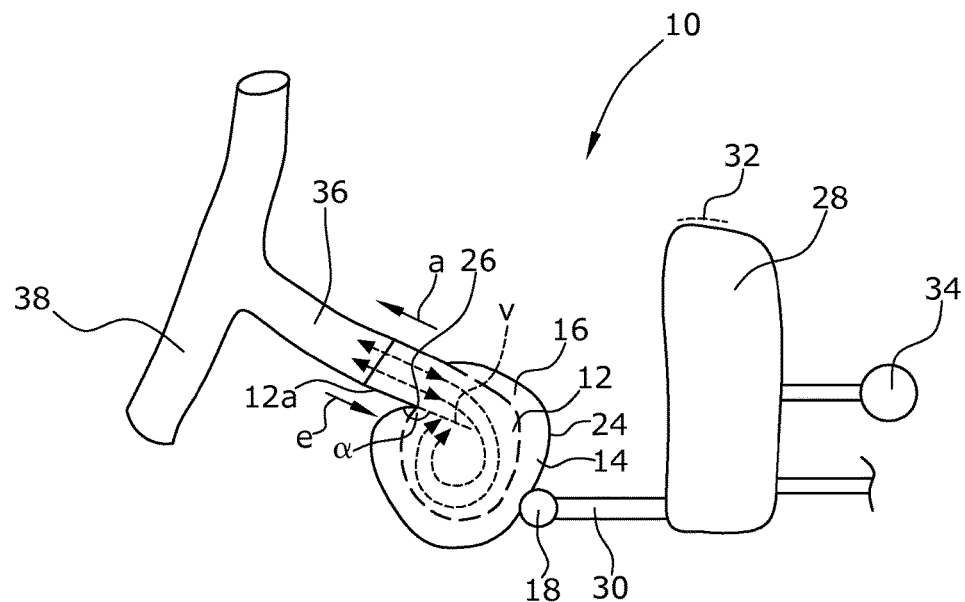
FIG. 1 is a schematic illustration of a first embodiment of the device of the present disclosure.

As illustrated in FIG. 1, the portable dialysis device 10 of the present disclosure comprises an incompressible housing 24 designed in a flow-optimized manner. The housing 24 accommodates the blood chamber 12 and the hydraulic chamber 14 which are separated from each other by the filter and delivery membrane 16. At the end of its inlet-side incompressible section 12a, the housing 24 has a flow breakaway edge 26. At this point, the housing widens abruptly at an angle α larger than 90°. The blood flow caused and enhanced thereby, is represented by dotted lines in FIG. 1.

In FIG. 1, the reference numeral 30 identifies a hydraulic line for supplying hydraulic fluid into the hydraulic chamber and from the same. The pump 18 is arranged between the hydraulic chamber 14 and the hydraulic line 30. At the other end of the hydraulic line 30, the reservoir 28 is arranged which includes a filter 32 for excreting water and a port 34 for puncturing liquid.

The blood chamber 12 is connected to a blood vessel 38, e. g. the aorta of the patient, by means of a vascular prosthesis 36.

Through the inlet 12a, blood flows tangentially to the inner wall of the blood chamber 12 so that a favorable flow can be obtained. In this embodiment the blood chamber 12 has a common inlet and outlet.

The volume of liquid passing the filter membrane 16 may be 1 l to 2 l per 24 hours.

Figure 2:
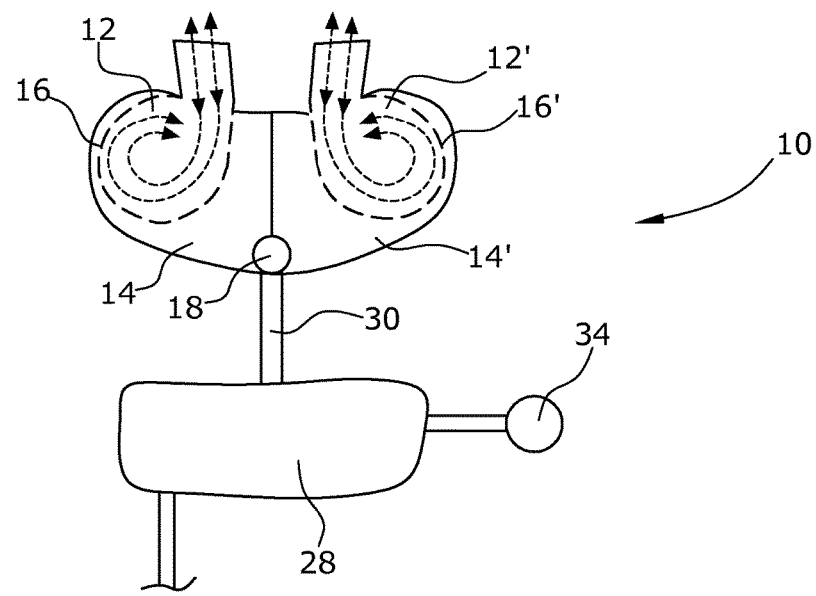
FIG. 2 is a schematic illustration of a second embodiment of the device of the present disclosure.

According to the embodiment illustrated in FIG. 2, the dialysis device 10 comprises a first and a second blood chamber 12, 12', a first and a second hydraulic chamber 14, 14', as well as a first and a second delivery membrane 16, 16'. The pump 18 is used to alternately or simultaneously fill and empty the hydraulic chambers 14, 14' with hydraulic fluid. In this embodiment the two delivery membranes 16, 16' may comprise different pore sizes.

Figure 3:
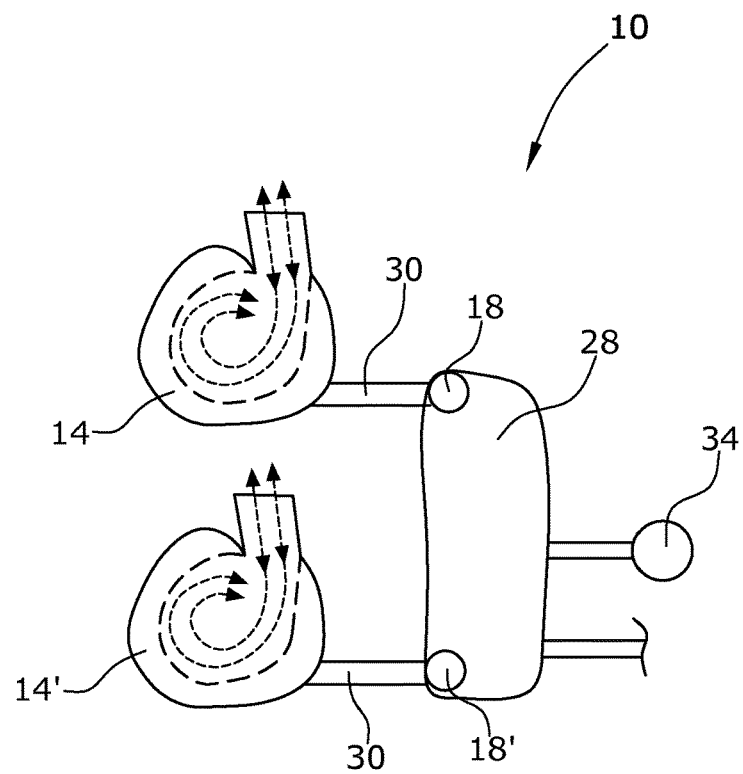
FIG. 3 is a schematic illustration of a third embodiment of the device of the present disclosure.

FIG. 3 is similar to the embodiment in FIG. 2, although two pumps 18, 18' are used instead of a single pump to pump the hydraulic fluid from the reservoir 28 into the hydraulic chambers 14, 14' and back.

Figure 4:
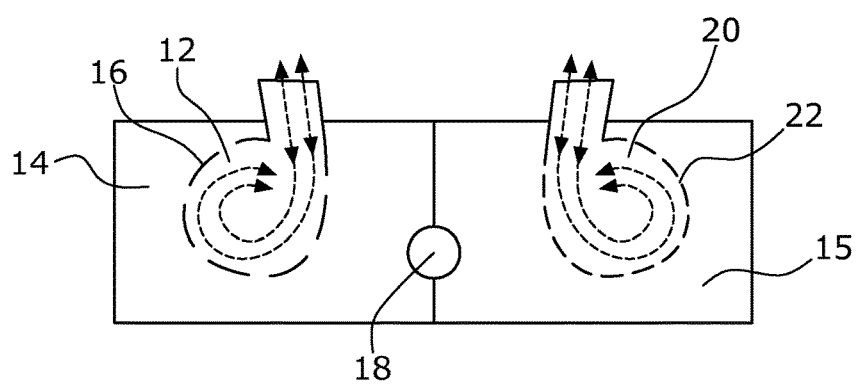
FIG. 4 is a schematic illustration of a fourth embodiment of the device of the present disclosure.

In the embodiment in FIG. 4, the blood chamber 14 is surrounded by a delivery membrane 16 having a rather large pore size through which the substances can pass that are meant to return into the blood circulation. In this case, too, the blood chamber 12 is compressed by the hydraulic fluid 14. The hydraulic fluid is conveyed by the pump 18. On the right hand side of the device in FIG. 4, the second hydraulic chamber 15 is provided which may be fluidically separated from the hydraulic chamber 14. Thus, the pump 18 alternately conveys the hydraulic fluid from the first hydraulic chamber 14 to the second hydraulic chamber 15 and back. When pumping the hydraulic fluid into the second hydraulic chamber 15, the secondary dialysate chamber 20 is compressed by the filter membrane 22. The same simultaneously serves as a filter membrane and has a smaller pore size than the filter membrane 16.

As illustrated in FIG. 5, the blood chamber 12 and the hydraulic chamber 14 can take various forms. For example, it is possible to compress the blood chamber 12 from both sides by making the hydraulic chamber 14 surround the blood chamber 14. This can be seen in FIGS. 5a to 5d. The compressed state of the blood chamber 12 is illustrated by dotted lines in FIG. 5a.

Figure 5A:
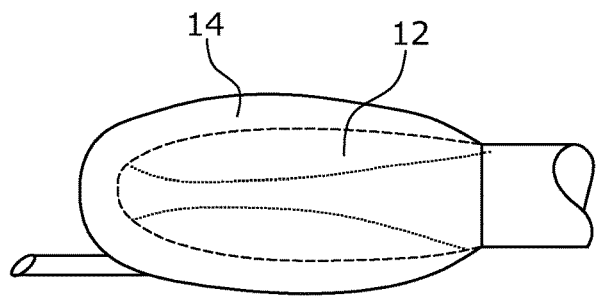
FIG. 5 illustrates various embodiments of a delivery membrane.
Figure 5B:
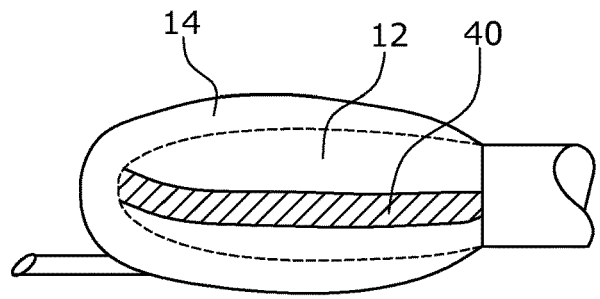
Figure 5C:
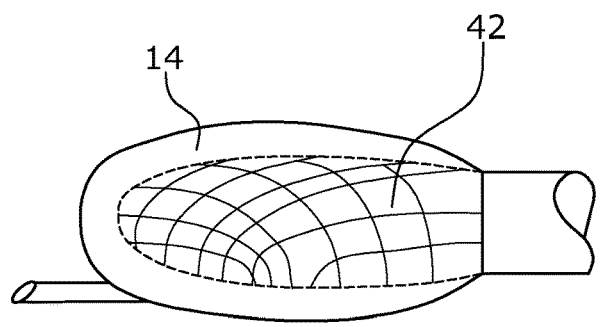
Figure 5D:
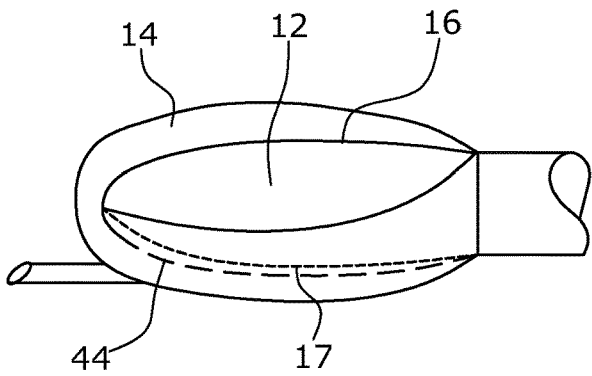

According to FIG. 5a, an equator-shaped section 40 of the blood chamber 12 is formed from reinforced tissue so that the membrane of the blood chamber 12 can be supported. As an alternative, it is possible to provide a supporting structure in the form of a net 42 as in FIG. 5c. The net 42 can be partially or completely connected firmly with the delivery membrane 16. Preferably, the net is flexible. As illustrated in FIG. 5d, a part of the delivery membrane 16 may be supported by a rigid supporting element 44 so that the pumping process takes place only in the flexible upper section of the delivery membrane 16.

What is claimed is:

1. A portable dialysis device that can be continuously worn in and/or on the body of a patient, comprising:
a blood chamber in which blood of the patient can be received,
a hydraulic chamber which can be filled with a hydraulic fluid and which adjoins the blood chamber,
an at least partially flexible delivery membrane which is arranged between the hydraulic chamber and the blood chamber and which, when the hydraulic chamber is filled with hydraulic fluid, is movable in a direction of the blood chamber in such a way as to cause a compression of the blood chamber and therefore an ejection of the blood located therein, a pump for controllable filling and/or emptying of the hydraulic fluid in the hydraulic chamber, such that the blood can be conveyed into the blood chamber and/or out of the blood chamber, a filter membrane which is arranged between the blood chamber and the hydraulic chamber and through which waste substances in the blood can be removed to the hydraulic fluid located in the hydraulic chamber, by (1) a concentration gradient between the blood and the hydraulic fluid and (2) ultrafiltration using a pressure gradient between the blood and the hydraulic fluid, such that the hydraulic fluid serves at the same time as dialysate; and an implantable or partially implantable reservoir for receiving a larger volume of the hydraulic fluid serving as the dialysate than the hydraulic chamber receives, wherein the hydraulic fluid is pumped from the reservoir to the hydraulic chamber and back by the pump, the pump being arranged between the hydraulic chamber and the reservoir such that, when the hydraulic fluid is conveyed from the reservoir to the hydraulic chamber, a concentration of waste substances in the dialysate contained in the hydraulic chamber is reduced, and wherein the reservoir comprises a discharge device for discharging dialysate from the reservoir, which is designed as a connection to a urinary system and/or a colon of the patient, wherein the blood chamber and the hydraulic chamber are arranged in an incompressible housing, and the blood chamber comprises an incompressible section at an inlet side, which at a downstream end thereof, seen in a direction of the blood inlet flow (e), is formed with a flow breakaway edge at which the blood chamber widens abruptly at an angle ($\alpha$) of at least 90 degrees relative to an extension (v) of the incompressible section, wherein the blood flows tangentially along an inner wall of the blood chamber through the inlet side, so that a return flow of the blood from the blood chamber is enhanced, while avoiding dead points in the flow in the blood chamber, wherein said dead points may cause the formation of thrombi.

2. The portable dialysis device of claim 1, wherein the filter membrane and the delivery membrane are a common membrane that at the same time compresses the blood chamber and filters the blood.

3. The portable dialysis device of claim 1, wherein the filter membrane and the delivery membrane are separate components and the filter membrane is inflexible.

4. The portable dialysis device of claim 1, wherein the pump has a rotary direction that is reversible and a volume flow of the hydraulic fluid conveyed by the pump is controllable, so that the blood can be conveyed in a defined volume flow into and out of the blood chamber by or assisted by the pump.

5. The portable dialysis device of claim 1, wherein by controlling a volume flow of the hydraulic fluid conveyed by the pump, the pressure gradient between the blood and the hydraulic fluid serving as the dialysate can be adjusted to control the blood purification by ultrafiltration, by setting a higher or a lower pressure in the hydraulic chamber than in the blood chamber.

6. The portable dialysis device of claim 1, wherein the pump provides a continuous uninterrupted conveying of the blood into the blood chamber and out of the blood chamber, wherein the blood conveyed into the blood chamber has a volume flow that is 0.4 l to 2.5 l per minute for adult patients and 50 ml to 800 ml per minute for children.

7. The portable dialysis device of claim 1, further comprising a second blood chamber, a second hydraulic chamber, a second delivery membrane, and a second filter membrane, which cooperate in a manner corresponding to the first blood chamber, the first hydraulic chamber, the first delivery membrane, and the first filter membrane, wherein the pump can alternately or simultaneously convey the hydraulic fluid into and out of the first and second hydraulic chambers so that a simultaneous or alternate compression and expansion of the first and second blood chambers occurs, wherein the first and second filter membranes have pore sizes that differ from each other.

8. The portable dialysis device of claim 1, further comprising at least one sensor for determining a systole in circulation of the patient such that a supply of the blood into the blood chamber occurs during the systole.

9. The portable dialysis device of claim 1, further comprising a rigid pressure plate arranged between the blood chamber and the hydraulic chamber, which is displaceable from the hydraulic chamber towards the blood chamber as the hydraulic chamber is filled with the hydraulic fluid, so that the pressure plate causes a compression of the blood chamber.

10. The portable dialysis device of claim 1, further comprising a charge generator device for the generation of an electric charge in the filter membrane so that waste products in the hydraulic fluid are repelled by the electric charge and are prevented from flowing towards the filter membrane.

11. The portable dialysis device of claim 1, wherein the hydraulic chamber adjoining the blood chamber is a first hydraulic chamber and that, by a pump, the hydraulic fluid can be conveyed from the first hydraulic chamber into a second hydraulic chamber and back, wherein the second hydraulic chamber adjoins a secondary dialysate chamber and is separated therefrom by a second filter membrane through which waste products can be discharged from the hydraulic fluid serving as the dialysate to the secondary dialysate in the secondary dialysate chamber.

12. The portable dialysis device of claim 1, wherein the inner wall of the blood chamber is arcuate along an entire length of the inner wall.

13. The portable dialysis device of claim 1, wherein the blood chamber has an arcuate configuration.

14. The portable dialysis device of claim 1, wherein the angle ($\alpha$) is larger than 90 degrees relative to the extension (v) of the incompressible section.

* * * * *